United States Patent
Wang et al.

(10) Patent No.: US 9,784,733 B1
(45) Date of Patent: Oct. 10, 2017

(54) RAPID DIAGNOSTIC TEST DEVICE BY DRIVEN FLOW TECHNOLOGY

(71) Applicant: DNT SCIENTIFIC RESEARCH, LLC, San Diego, CA (US)

(72) Inventors: Naishu Wang, Poway, CA (US); Michael Chang Chien, Cerritos, CA (US)

(73) Assignee: DNT SCIENTIFIC RESEARCH, LLC, San Diego, CA (US)

( * ) Notice: Subject to any disclaimer, the term of this patent is extended or adjusted under 35 U.S.C. 154(b) by 0 days.

(21) Appl. No.: 15/630,174

(22) Filed: Jun. 22, 2017

(51) Int. Cl.
  *G01N 33/558* (2006.01)
  *G01N 33/53* (2006.01)
  *B01L 3/00* (2006.01)
  *G01N 21/78* (2006.01)
  *G01N 21/77* (2006.01)

(52) U.S. Cl.
  CPC ............ *G01N 33/53* (2013.01); *B01L 3/5027* (2013.01); *G01N 21/78* (2013.01); *G01N 33/558* (2013.01); *G01N 2021/7759* (2013.01); *G01N 2021/7763* (2013.01)

(58) Field of Classification Search
  CPC .................................................. G01N 33/558
  USPC ........................................ 422/401, 420, 425
  See application file for complete search history.

(56) References Cited

U.S. PATENT DOCUMENTS

| | | | |
|---|---|---|---|
| 4,299,916 A | 11/1981 | Litman et al. | |
| 4,366,241 A | 12/1982 | Tom et al. | |
| 5,352,410 A | 10/1994 | Hansen et al. | |
| 5,403,551 A * | 4/1995 | Galloway | A61B 10/007 422/417 |
| 5,656,503 A | 8/1997 | May et al. | |
| 6,140,136 A | 10/2000 | Lee | |
| 6,372,514 B1 * | 4/2002 | Lee | G01N 33/54366 422/408 |
| 6,379,620 B1 * | 4/2002 | Tydings | A61B 10/0096 422/412 |
| 6,403,383 B1 | 6/2002 | Casterlin et al. | |
| 6,730,268 B2 * | 5/2004 | Lee | A61B 10/0096 422/417 |
| 6,805,837 B2 * | 10/2004 | Tydings | A61B 10/0096 422/412 |
| 6,875,185 B2 | 4/2005 | Wong et al. | |
| 7,431,882 B2 | 10/2008 | Parker | |
| 7,741,103 B2 | 6/2010 | Guirguis | |
| D626,249 S | 10/2010 | Wang et al. | |

(Continued)

OTHER PUBLICATIONS

Office Action dated Aug. 25, 2017 from related U.S. Appl. No. 15/620,216.

*Primary Examiner* — Chris L Chin
(74) *Attorney, Agent, or Firm* — Innovation Capital Law Group, LLP; Vic Lin

(57) ABSTRACT

A rapid diagnostic test device uses driven flow technology to significantly expedite the testing time of a sample. The rapid diagnostic test device can be used to analyze liquids, such as some body fluids, by using labeled molecular affinity binding, such as immunochromatography. The test device can detect an analyte, such as an antibody or antigen, which may indicate a particular condition, the presence of a particular drug, or the like. The device includes an inner member that receives the body fluid. Dripping holes in the inner member, or a sloped surface, creates a stream force of the body fluid against the sample pad of the test strip. A portion of the stream force of the body fluid is directed upward toward the conjugate pad to push the antibody/body fluid sample onto the membrane of the test strip.

9 Claims, 14 Drawing Sheets

(56) References Cited

U.S. PATENT DOCUMENTS

| | | |
|---|---|---|
| 7,879,623 B2 | 2/2011 | Guirguis |
| 7,981,382 B2 | 7/2011 | Wong et al. |
| 8,021,625 B2 | 9/2011 | Wang et al. |
| 8,163,253 B1 * | 4/2012 | Hartselle ............ A61B 10/0096 422/400 |
| 8,206,661 B2 * | 6/2012 | Vallejo ................ A61B 10/007 422/401 |
| 8,394,626 B2 * | 3/2013 | Ramsey ............... A61B 10/007 422/400 |
| 8,889,424 B2 | 11/2014 | Ehrenkranz et al. |
| 8,916,390 B2 | 12/2014 | Ozcan et al. |
| 8,940,527 B2 * | 1/2015 | Guirguis ............ A61B 10/0051 422/400 |
| 8,992,855 B2 * | 3/2015 | Lin .................... A61B 10/0096 422/405 |
| 9,377,457 B1 | 6/2016 | Wang et al. |
| 9,414,813 B2 | 8/2016 | Engel et al. |
| 9,535,061 B1 * | 1/2017 | Wang .................. G01N 33/558 |
| 2004/0152206 A1 | 8/2004 | Davis et al. |
| 2005/0163660 A1 | 7/2005 | Wang |
| 2006/0292700 A1 | 12/2006 | Wang et al. |
| 2007/0065339 A1 | 3/2007 | Huff |
| 2007/0259442 A1 | 11/2007 | Gould et al. |
| 2008/0199851 A1 | 8/2008 | Egan et al. |
| 2009/0208371 A1 | 8/2009 | Hannant et al. |
| 2010/0278692 A1 * | 11/2010 | Chen ...................... B01L 3/508 422/420 |
| 2013/0022517 A1 | 1/2013 | Engel et al. |
| 2015/0173742 A1 | 6/2015 | Palese et al. |
| 2015/0203904 A1 | 7/2015 | Hopper |
| 2015/0211987 A1 | 7/2015 | Burg et al. |
| 2016/0025752 A1 | 1/2016 | Santiago et al. |

* cited by examiner

RAPID DIAGNOSTIC TEST DEVICE BY DRIVEN FLOW TECHNOLOGY

BACKGROUND OF THE INVENTION

1. Field of the Invention

One or more embodiments of the invention relate generally to apparatus for analyzing liquids, such as body fluids, using labeled molecular affinity binding, such as immunochromatography. More particularly, the invention relates to strip test apparatus for detecting an analyte, such as an antibody or antigen, which may indicate a particular condition.

2. Description of Prior Art and Related Information

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon.

Labeled molecular affinity binding, such as immunochromatographic assays, have existed for decades and have proven to be an inexpensive way to screen for various conditions, such as abused drugs, and other conditions, such as pregnancy and cancer, or for single or multiple pathogenic conditions, such as HIV infection.

In the point-of-care test (POCT) setting, immunochromatographic assays are typically conducted using lateral flow strip technology as described in May et al., U.S. Pat. No. 5,656,503, incorporated herein by reference. With lateral flow devices, antibodies are movably supported on a solid support, such as a porous pad. Antigen derivatives are deposited as immobilized indicator lines downstream of the antibodies, whereby the target antigens in a fluid sample flow laterally as a liquid matrix by capillary action through the solid support. The antibodies are normally colored for visual indication. The fluid sample carries the antibodies downstream towards the indicator lines of immobilized antigen derivatives while a reaction takes place between the target antigens and the antibodies. Any antibodies that have not reacted with the antigen in the sample bind to the antigen derivatives at the indicator lines. When little or no target antigen is present in the sample, most or all of the colored antibodies are carried downstream to the indicator lines of the immobilized antigen derivatives. At the immobilized antigen derivatives, the colored antibodies bind together with the antigen derivatives in such concentrations that the colorant of the antibodies becomes readily visible. It is also known that the antigen derivatives' and the antibodies' roles can be interchanged. That is, the antigen derivatives can be labeled with colorant and movably placed in the solid support while the antibodies are placed as immobilized deposited indicator lines downstream.

Unfortunately, although they can be inexpensive and simple-to-use, depending on the type of condition being detected, these tests typically take from about 5 to 20 minutes to complete and provide a typical accuracy of between 75% and 95%, falling short of the 99% or above accuracy generally considered to be necessary for a confirmatory test. Moreover, these conventional tests provide no objective measure of a quantitative result, such as the concentration of a given drug present in the liquid being tested.

The reasons for the insufficient accuracy in many rapid in vitro diagnostic (IVD) test devices are primarily due to their current lack of overall higher sensitivity and specificity. Different samples may contain chemicals or particles which inhibit the rapid and well mixed liquid flow or otherwise interfere with one or both of the first and second affinity binding reactions.

Other prior devices have attempted to enhance sensitivity or specificity by pretreating various parts of the device with reaction or flow enhancing reagents, pH conditioning chemicals, or even non-specific adhesive blocking molecules which will "block-out" non-analyte molecules which might cause non-specific adhesion, or otherwise compete with the analyte in question for specific binding members, especially in the reaction zones region of the strip. These attempts have met with limited success in some types of testing, but do not provide the desired accuracy in many others. Also, pretreatment with two or more of the above pretreatments exacerbates the difficulties in obtaining uniform manufacturing due to potential incompatibilities between the pretreatment chemicals. For example, the pH conditioner might disrupt the effectiveness of the non-specific blocking member molecules. Moreover, the manufacturing step of pretreating with a second pretreatment chemical can dislodge some of the first pretreatment chemical.

Further, lot-to-lot variation in the manufacture of many IVD test devices can often lead to ambiguous results, such as false negatives as well as weak false positives, so-called "ghostlines" or "phantom lines". False negatives typically occur when non-specific molecules interfere with the first and/or second affinity binding actions. It has been found that non-analyte molecules can clump together in liquid samples that are not well mixed so that they temporarily prevent access between analytes and binding members. Even temporary interference in past devices can prevent an adequate number of labeled analyte complexes and/or ultimately immuno-sandwich complexes from forming. In this way, if a non-analyte molecule or clump of molecules blocks access between analytes and binding members for only a few seconds, it may be enough to induce a false negative result. Further, clumps of non-analyte molecules can carry an overabundance of the labeled mobilizable binding members to the second affinity binding site to generate a false positive result.

Lateral flow devices are useful due to their low cost and ease of use. However, prior lateral flow devices suffer from low accuracy and relatively long test wait times as detailed above. This is especially true for saliva testing because of the low concentrations of analytes present. Current lateral flow strips cannot provide the necessary sensitivity and specificity within the time normally allotted to a typical law enforcement action such as a traffic stop.

The low accuracy can be due to a number of problems unique to lateral flow-type tests. First, there is often uneven movement of the immuno-particles within the nitrocellulose membrane. Smaller, non-analyte molecules mix together with the larger analyte molecules and compete for sites, often preventing the larger molecules from reacting in the desired fashion.

Therefore, there is a need to improve the accuracy of rapid IVD test devices so that rapid, inexpensive, easily conducted and quantitative immunological testing becomes a reality.

SUMMARY OF THE INVENTION

Embodiments of the present invention provide a device for testing a liquid sample for the concentration of at least one analyte comprising a stream generation mechanism for generating a stream of a liquid sample; a test strip slot configured to retain a test strip as a location such that the stream impinges a sample pad of the test strip; and a compressing member positioned adjacent a conjugate pad of the test strip when the test strip is placed in the test strip slot.

In some embodiments, the stream generation mechanism can include an outer chamber; an inner chamber fitting into the outer chamber, the inner chamber receiving the liquid sample therein; and a plurality of dripping holes formed in a lower portion of the inner chamber, the plurality of dripping holes permitting the liquid sample introduced to the inner chamber to flow as the stream out of the inner chamber.

In some embodiments, the stream generation mechanism can include a base having a base main portion and a base slide portion, the base slide portion extending at a first angle from the base main portion; a top member fitting onto the base, the top member having a top member main portion and a top member slide portion, the top member slide portion extending at a second angle from the top member main portion; and a sampling inlet formed between the base slide portion and the top member slide portion, the sampling inlet receiving the liquid sample therein and directing the liquid sample toward a sample pad of a test strip as the stream when the test strip is disposed in test strip slots of the base.

Embodiments of the present invention provide a device for testing a liquid sample for the concentration of at least one analyte, comprising an outer chamber; an inner chamber fitting into the outer chamber, the inner chamber receiving the liquid sample therein; a plurality of dripping holes formed in a lower portion of the inner chamber, the plurality of dripping holes permitting the liquid sample introduced to the inner chamber to flow as a stream out of the inner chamber; a plurality of test strip slots for retaining a plurality of test strips therein, wherein the test strip slots are positioned such that when test strips are positioned in the test strip slots, a sample pad of the test strip is impacted by the stream; and a compressing member positioned adjacent conjugate pad of the test strip when the test strip is placed in the test strip slot.

Embodiments of the present invention further provide a test system for testing a liquid sample for the concentration of at least one analyte, comprising a plurality of test strips, each comprising a sample pad receiving the liquid sample; a conjugate pad including a gold colloid of antibody; and a membrane including an antigen test line; and a test device comprising an outer chamber; an inner chamber fitting into the outer chamber, the inner chamber receiving the liquid sample therein; a plurality of dripping holes formed in a lower portion of the inner chamber, the plurality of dripping holes permitting the liquid sample introduced to the inner chamber to flow as a stream out of the inner chamber and onto the sample pad of each of the plurality of test strips; a plurality of test strip slots retaining the plurality of test strips therein; and a compressing member positioned adjacent conjugate pad of the test strip.

Embodiments of the present invention also provide a method for testing for an analyte in a sample, comprising disposing a plurality of tests strips into test strip slots of an inner chamber; placing the inner chamber into the outer chamber; introducing the sample into the inner chamber, wherein the sample flows as a stream out of a plurality of dripping holes formed at a bottom of the inner chamber, the stream impacting a sample pad of each of the plurality of test strips, the stream causing an upward flow directed to a conjugate pad of the test strip, the conjugate pad containing a gold colloid of antibody; and positioning a compressing member adjacent the conjugate pad, the compressing member positioned to cause the upward flow to move the gold colloid of antibody onto a membrane of the test strip.

Embodiments of the present invention further provide a device for testing a liquid sample for the concentration of at least one analyte comprising a base having a base main portion and a base slide portion, the base slide portion extending at a first angle from the base main portion; a top member fitting onto the base, the top member having a top member main portion and a top member slide portion, the top member slide portion extending at a second angle from the top member main portion; a sampling inlet formed between the base slide portion and the top member slide portion, the sampling inlet receiving the liquid sample therein and directing the liquid sample toward a sample pad of a test strip as a stream when the test strip is disposed in test strip slots of the base; and a compressing member positioned adjacent conjugate pad of the test strip when the test strip is placed in the test strip slot.

These and other features, aspects and advantages of the present invention will become better understood with reference to the following drawings, description and claims.

BRIEF DESCRIPTION OF THE DRAWINGS

Some embodiments of the present invention are illustrated as an example and are not limited by the figures of the accompanying drawings, in which like references may indicate similar elements.

Figure 1:
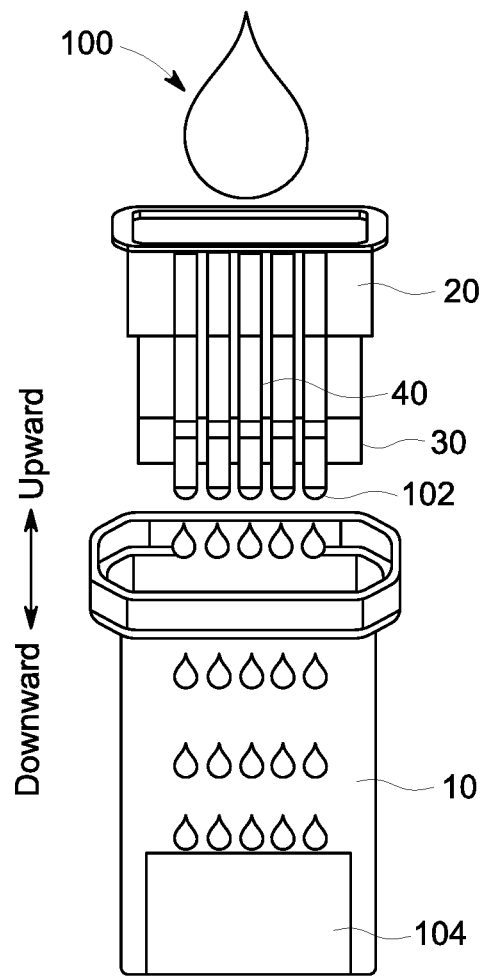
FIG. 1 illustrates an unassembled side view of a cup format rapid diagnostic testing device according to an exemplary embodiment of the present invention.

Unless otherwise indicated illustrations in the figures are not necessarily drawn to scale.

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS AND BEST MODE OF INVENTION

The terminology used herein is for the purpose of describing particular embodiments only and is not intended to be limiting of the invention. As used herein, the term "and/or" includes any and all combinations of one or more of the associated listed items. As used herein, the singular forms "a," "an," and "the" are intended to include the plural forms as well as the singular forms, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof.

Unless otherwise defined, all terms (including technical and scientific terms) used herein have the same meaning as commonly understood by one having ordinary skill in the art to which this invention belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the invention, it will be understood that a number of techniques and steps are disclosed. Each of these has individual benefit and each can also be used in conjunction with one or more, or in some cases all, of the other disclosed techniques. Accordingly, for the sake of clarity, this description will refrain from repeating every possible combination of the individual steps in an unnecessary fashion. Nevertheless, the specification and claims should be read with the understanding that such combinations are entirely within the scope of the invention and the claims.

In the following description, for purposes of explanation, numerous specific details are set forth in order to provide a thorough understanding of the present invention. It will be evident, however, to one skilled in the art that the present invention may be practiced without these specific details.

The present disclosure is to be considered as an exemplification of the invention, and is not intended to limit the invention to the specific embodiments illustrated by the figures or description below.

As is well known to those skilled in the art, many careful considerations and compromises typically must be made when designing for the optimal configuration of a commercial implementation of any device, and in particular, the embodiments of the present invention. A commercial implementation in accordance with the spirit and teachings of the present invention may be configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

The instant embodiments are useful to rapidly determine the presence of an analyte in a liquid sample at a concentration which confirms the condition being tested. The sample can include, for example, body fluids, such as whole blood, serum, plasma, urine, spinal fluid, amniotic fluid, mucous, saliva, and the like, or other fluids used in certain food and environmental testing.

As used herein, the term "analyte" refers to a compound or composition to be measured. The analyte can be any substance, such as an antigen or ligand, for which there exists a naturally or genetically occurring specific binding member, for instance, a binding molecule such as an antibody or receptor, and other molecules that exhibit the so-called "lock-in-key" pairing function.

Analytes also includes any antigenic substances, haptens, antibodies, and combinations thereof. The analyte can include a protein; a peptide; an amino acid; a ligand; a hormone; asteroid; a vitamin; a drug, including those administered for therapeutic purposes as well as those administered for illicit purposes; a pathogen; and an exogenious infectious microbe, such as a bacterium, a virus, and metabolites of or antibodies to any of the above substances. The analyte can also comprise an antigenic marker or antibody or receptor.

The precise nature of a number of analytes, together with a number of examples thereof are disclosed in Litman, et al., U.S. Pat. No. 4,299,916, issued Nov. 10, 1981; and Tom, et al., U.S. Pat. No. 4,366,241, issued Dec. 28, 1982, each of which are herein incorporated by reference in their entirety. Certain improved accuracy devices are disclosed in U.S. Pat. No. 8,021,625 (Wang et al.), which is incorporated herein by reference in its entirety.

The signal provided to the user of the device is provided by accumulation of a visually detectable label, such as a specific antigen pre-coated on a nitrocellulose membrane of a test strip, conjugated to a mobilizable binding member such as a specific antibody and/or antigen; ligand and/or receptor. This mobilizable binding member is sometimes referred to as a "binding member molecule", "a first affinity binding member", "labeled binding member" or simply "conjugate". In the instant embodiments, labels that produce a readily detectable signal are used. Thus, the instant embodiments provide colored labels which permit visible detection of the assay results without the addition of further substances and/or without the aid of instrumentation. However, in some embodiments, instrumentation may be used to provide a comparative or quantitative representation of the concentration of analyte in the sample.

The test strips described in these embodiments can include regions or pads that may include a dry, porous material. By "porous" it is meant that the matrix of material forming the porous structure allows liquids to flow through it.

As used herein, the term "sample pad" or "fluid collector" means the part of the assay device which is in direct contact with the liquid sample first during test operation, i.e., it receives the sample to be tested for the analyte in question. The fluid collector may be made of porous material, such as porous paper, cotton, cellulose, mixed fibers, glass fiber, polyester fiber, and the like.

The term "conjugate pad" or "conjugate color pad", as used herein, refers to the part of the assay device which is in liquid flow contact with the porous material of fluid collector. The contact can be an overlap or end-to-end connection, such that the liquid sample can migrate via wicking action or by surface tension-based forces such as capillary forces from the fluid collector through the conjugate pad. The conjugate pad comprises a porous material and a mobilizable labeled reagent, such as a gold colloid of antibody, that is capable of binding the analyte in question to form a labeled reagent-analyte complex which then migrates via liquid flow with the liquid sample along the pad.

The term "mobilizable" as referred to herein means diffusively or non-diffusively attached, or impregnated. The mobilizable reagents are capable of dispersing with the liquid sample and carried by the liquid sample in the liquid flow.

In one exemplary embodiment, drugs of abuse ("DOA") can be detected as a putative target analyte in a fluid specimen, such as urine. Those skilled in the art will readily appreciate adaptation of these embodiments to detect other analytes indicative of other pathogens, or pathogenic conditions in body, drugs of abuse ("DOA"), human immunodeficiency virus ("HIV"), food or environmental fluid specimens, and the like.

Further the exemplary embodiments will be described in connection with an immunochromatographic assay based on antigen/antibody binding. Those skilled in the art will readily appreciate adaptation of these embodiments to other types of molecular affinity binding-based tests.

Broadly, embodiments of the present invention provide a rapid diagnostic test device that uses driven flow technology to significantly expedite the testing time of a sample. The rapid diagnostic test device can be used to analyze liquids, such as some body fluids, by using labeled molecular affinity binding, such as immunochromatography. The test device can detect an analyte, such as an antibody or antigen, which may indicate a particular condition, the presence of a particular drug, or the like. The device includes an inner member that receives the body fluid. Dripping holes in the inner member or, in some embodiments, a sloped surface creates a stream force of the body fluid against the sample pad of the test strip. A portion of the stream force of the body fluid is directed upward toward the conjugate pad to push the antibody/body fluid sample onto the membrane of the test strip.

Most rapid diagnostic test devices use lateral flow technology, which starts the specimen sampling at the end of the sample pad on the test strip. Then, the specimen is migrated by capillary action through the conjugate pad/membrane. This conventional technique typically requires a testing time of about five minutes. The main reason for this required testing time is because the slow migration speed by capillary action cannot release all the gold colloids completely in a very short time. The present invention addresses this issue by applying a "stream specimen" method Referring to FIGS. 1 and 2, a cup format rapid diagnostic testing device 10, also referred to as testing device 10, can include an outer cup 10 into which an inner cup 20 may be disposed. The inner cup 20 can retain a plurality of test strips 40. A compression ring 30 may be disposed at one end of the inner cup 20. Body fluid 100, such as urine can be collected directly from a user. In some embodiments, the user can directly fill the inner cup, or, in other embodiments, the body fluid may be collected in a secondary cup (such as a specimen cup, not shown) and transferred to the inner cup 20. The body fluid 100 may form a stream 102 that may be forced onto the sample pad 41 by passing through dripping holes 21 (see FIG. 3) formed in the inner cup 20.

Figure 2:
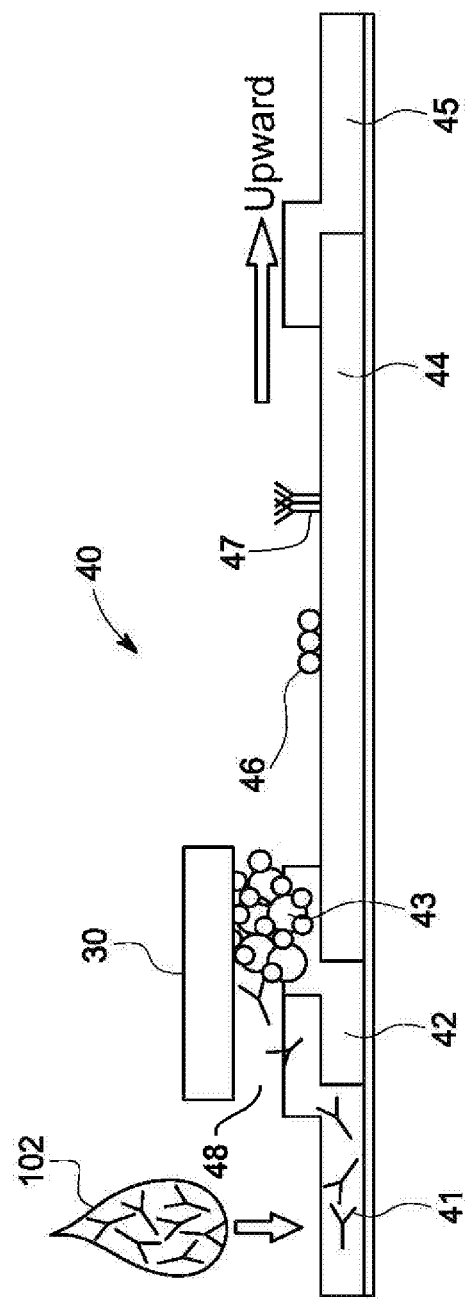
FIG. 2 illustrates a side, cross-sectional view of a test strip used in the cup format rapid diagnostic testing device of FIG. 1.
Figure 3:
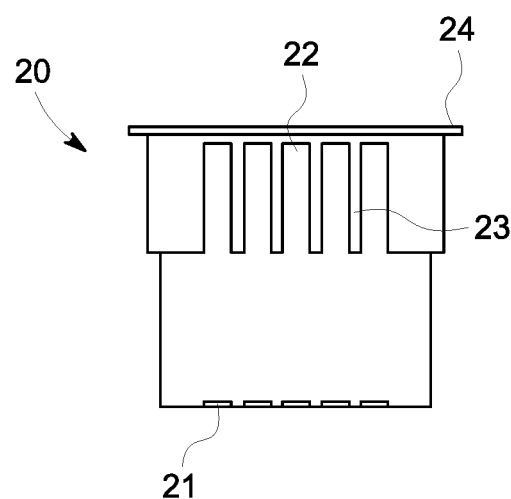
FIG. 3 illustrates a side view of an inner cup of the cup format rapid diagnostic testing device of FIG. 1.
Figure 4:
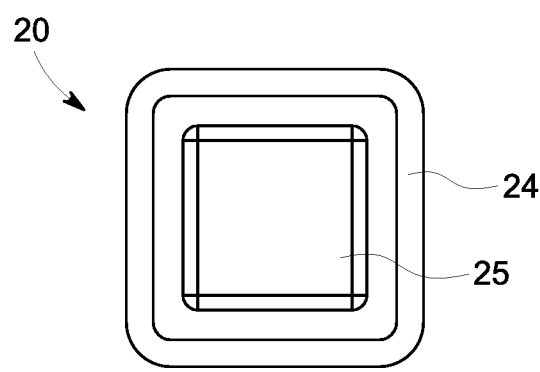
FIG. 4 illustrates a top view of the inner cup of FIG. 3.
Figure 5:
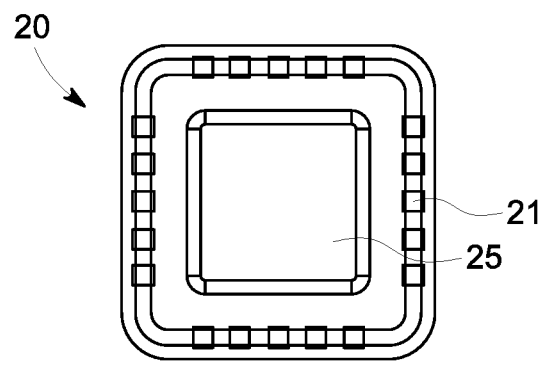
FIG. 5 illustrates a bottom view of the inner cup of FIG. 3.
Figure 6:
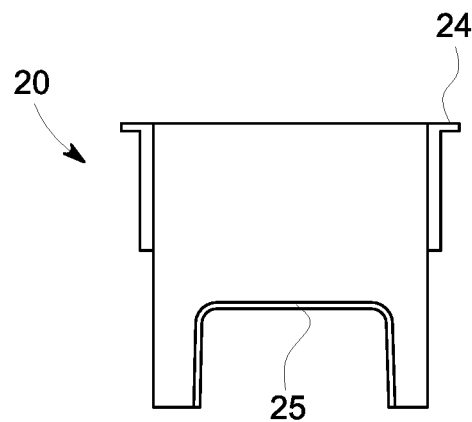
FIG. 6 illustrates a cross-sectional view taken along line VI-VI of FIG. 3.

The stream 102 may impact the sample pad 41 an angle of incidence that is typically from about 30 to about 150 degrees, for example, typically from about 70 to about 110 degrees, perhaps at about 90 degrees, as shown in FIG. 2. The stream 102 may precisely impact the sample pad 41 and divert its vector by refraction into upward and downward directions. The stream 102 that is directed downward will carry the specimen into the outer cup 10 which includes a reservoir 104 for retaining the specimen. The stream 102 that is directed upward will continue fluxing the conjugate pad 42 and push all the gold colloid of antibody 43 migrating onto the nitrocellulose membrane 44.

Another driving force can be generated from the compression ring 30, which is designed to have a certain gap 48 between the wall of the compression ring 30 and the conjugate pad 42. The gap 48 may be adjusted to optimize conditions and match with the upward stream force to drive all of the gold colloid 43 out of the conjugate pad 42 completely, typically within seconds.

In use, the stream 102 may contact the sample pad 41 and be driven to move all of the gold colloid 43 from the conjugate pad 42 onto the nitrocellulose membrane. The specimen/colloid mixture may contact an antigen test line 46 having the appropriate antigen placed thereon. When a substance of interest is present in the stream 102, the antigen test line 46 may visibly show the presence of the substance. A control line 47 may be disposed upward of the antigen test line 46 for providing a visible indicator when the specimen has reached this part of the membrane 44. An absorbent pad 45 may absorb any additional specimen reaching the end of the test strip 40.

Details of the inner cup 20 are shown in FIGS. 3 through 6. In some embodiments, the inner cup 20 may include a raised bottom portion 25 that permits the body fluid 100 to reach the dripping holes 21, while reducing the volume needed to fill the inner cup 20. A plurality of test strip slots 22 may be disposed between raised portions 23 on each side of the inner cup 20. The inner cup 20 may typically be formed as a square-shaped cup with an equal number of test strip slots 22 on each side of the inner cup 20. Of course, other shapes may be contemplated within the scope of the present invention. An upper lip 24 may be disposed about the open face of the inner cup 20. The upper lip 24 may contact the outer cup 10 when the inner cup 20 is positioned inside the outer cup 10, ready for a sample to be introduced.

The dripping holes 21 may be configured to correspond to each of the test strip slots 22, such that when a test strip 40 is disposed in the test strip slot 22, the sample pad 41 of the test strip 40 is disposed to receive the flow of the stream 102 from the dripping hole 21. The dripping holes 21 may have a width that is no less than the width of the test strip 40 (or the test strip slot 22) to drive all of the gold colloids 43 evenly. This feature can help provide an even colored antigen test line 46, allowing accurate reading thereof, especially when an electronic reader is used.

While the Figures show space for five test strips on each face, other sized are contemplated within the scope of the present invention.

Figure 7:
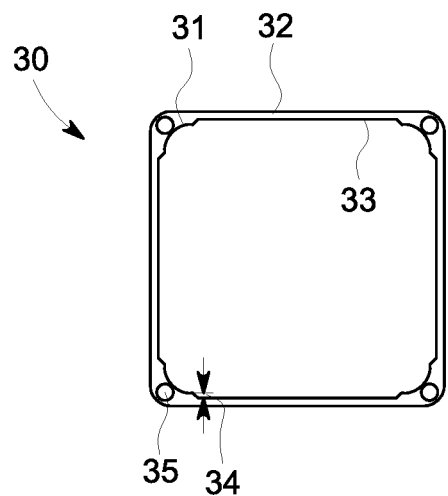
FIG. 7 illustrates a top view of a compression ring of the cup format rapid diagnostic testing device of FIG. 1.
Figure 8:
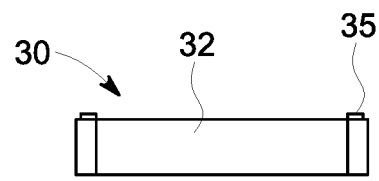
FIG. 8 illustrates a side view of the compression ring of FIG. 7.
Figure 9:
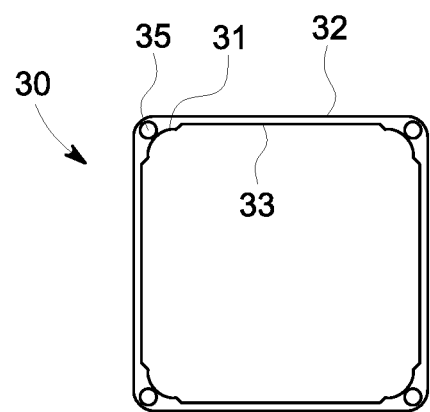
FIG. 9 illustrates a bottom view of the compression ring of FIG. 7.

FIGS. 7 through 9 show detailed views of the compression ring 30. The compression ring 30 may fit about the inner cup 20 at corner portions 31. The corner portions 31 may extend further inward than side portions 32, thus providing a gap 34 between the interior edge 33 of the side portions 32 and the corner portions 31. This gap 34 is optimized to apply the best compression force on the conjugate pad 42, as discussed above. The compression ring 30 may also be used to secure each test strip 40 without moving its position. Corner indexing protrusions 35 may fit into pillars 13 of the outer cup 10 (see FIG. 10) to support the compression ring 30 within the outer cup 10 and secure its position therein.

Figure 10:
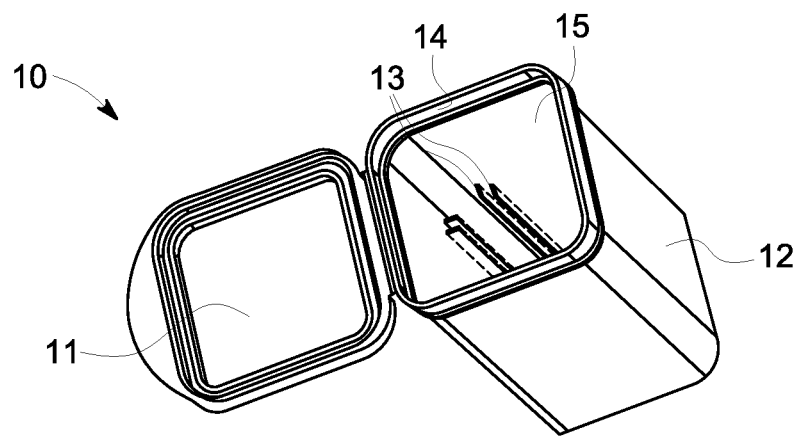
FIG. 10 illustrates a top perspective view of an outer cup of the cup format rapid diagnostic testing device of FIG. 1.
Figure 11:
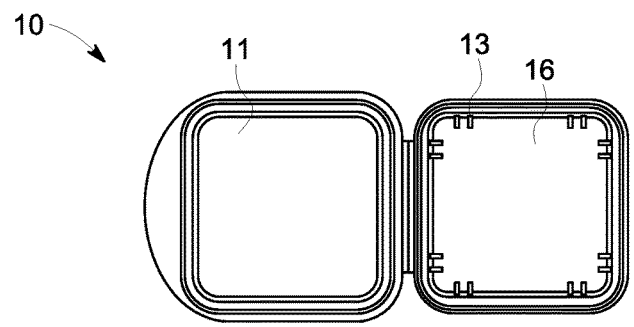
FIG. 11 illustrates a top view of the outer cup of FIG. 10.
Figure 12:
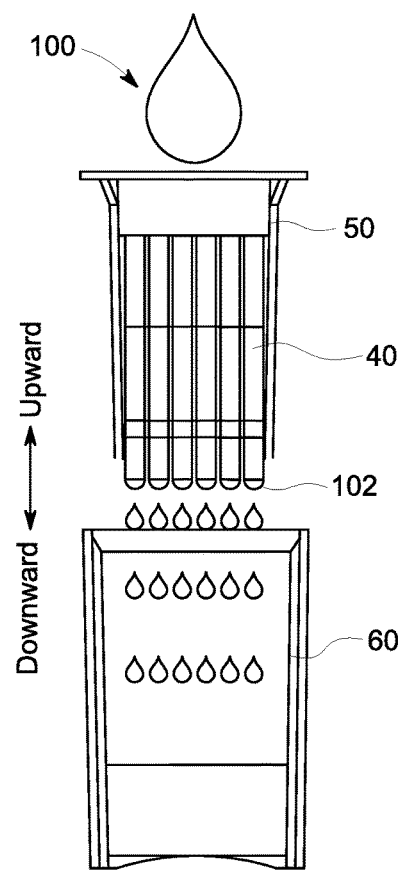
FIG. 12 illustrates an unassembled side view of a pour cassette format rapid diagnostic testing device according to an exemplary embodiment of the present invention.
Figure 13:
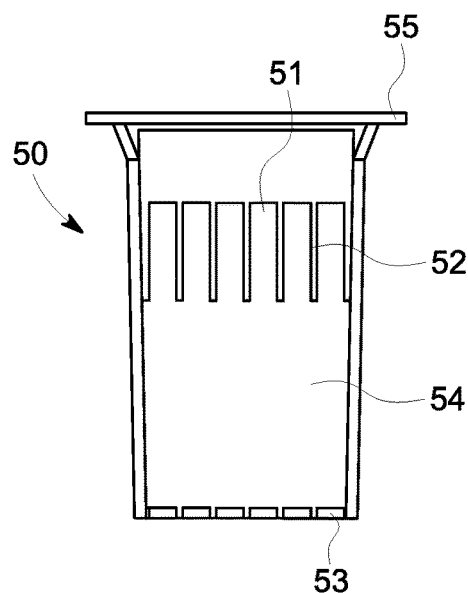
FIG. 13 illustrates a front view of a cassette of the pour cassette format rapid diagnostic testing device of FIG. 12.
Figure 14:
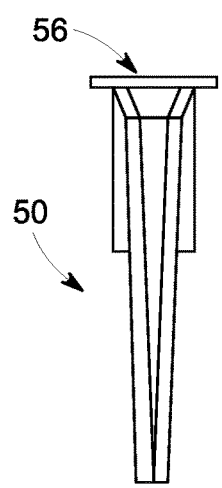
FIG. 14 illustrates a side view of the cassette of FIG. 13.
Figure 15:
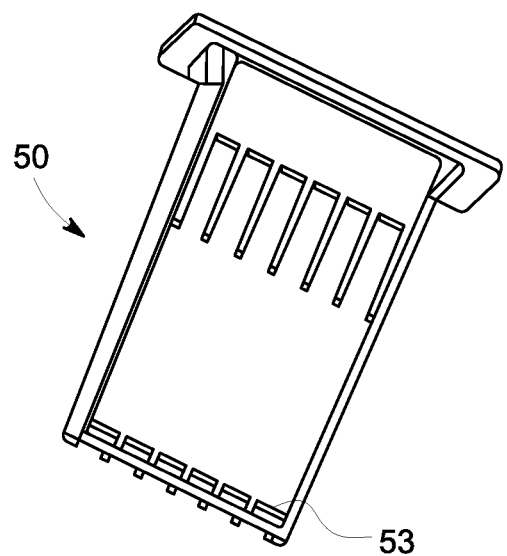
FIG. 15 illustrates a perspective view of the cassette of FIG. 13.

Referring additionally to FIGS. 10 and 11, a cap 11 may be disposed on the outer cup 10 to seal the outer and inner cups 10, 20 and avoid leakage. The testing device 10 may be assembled, with the testing strips 40 disposed in the test strip slots 22 and with the inner cup 20 disposed inside the outer cup 10 with the cap 11 closed, awaiting a sample.

The outer cup 10 may include a ledge 14 on which the upper lip 24 of the inner cup 20 may rest. The inside 15 of the outer cup 10 can contain the inner cup 20 and test strips 40 in both a pre-test configuration and during the testing process, after the body fluid 100 is introduced into the inner cup 20.

Sides 12 of the outer cup 10 may be transparent to permit visible access to the testing strips 40, allowing for user reading or machine reading of the test strips 40. A bottom 16 of the outer cup 10 may form the reservoir 104, discussed above, for holding additional sample if desired.

Referring now to FIGS. 12 through 19, a pour cassette rapid testing device 70 operates on a principle similar to the testing device 10 discussed above in that body fluid 100 is placed within a pour cassette 50, or simply cassette 50, having dripping holes 53 at the bottom to permit a stream 102 of the body fluid 100 to contact the sample pad 41 (see FIG. 2) of the test strip 40. Also, similar to the testing device 10, the testing device 70 includes an outer cup 60 that can collect fluid that is deflected downward from the stream 102.

The cassette 50 may be similar to the inner cup 20 discussed above, except that the cassette 50 is "double-sided", meaning that, instead of having test strips disposed on four sides, there are two sides of the cassette 50 having test strip slots 51 surrounded by raised regions 52 for holding the test strips 40. The test strips 40 may rest against the side wall 54 of the cassette 50. The cassette 50 may include an upper lip 55 disposed about an opening 56 to the interior of the cassette 50.

Conventional cassette format sampling methods use a pipette to transfer specimen directly onto the sample pad of the test strips. Every test strip requires 3-4 droplets in such a way to require a user to spend more sampling time when there are more test strips on the same device. A conventional dip format requires the user to hold the dipcard in fluid at least 10 seconds to let the sample pad absorb enough specimen. With the testing device 70 of the present invention, the user simply pours specimen into the cassette 50 in one second without holding the cassette or a pipette. The cassette 50 generates the stream 102 as discussed above with testing device 10. The stream 102 provides a force to continue fluxing the conjugate pad 42 to push all of the gold colloid 43 migrating on the membrane 44 (see FIG. 2).

Figure 16:
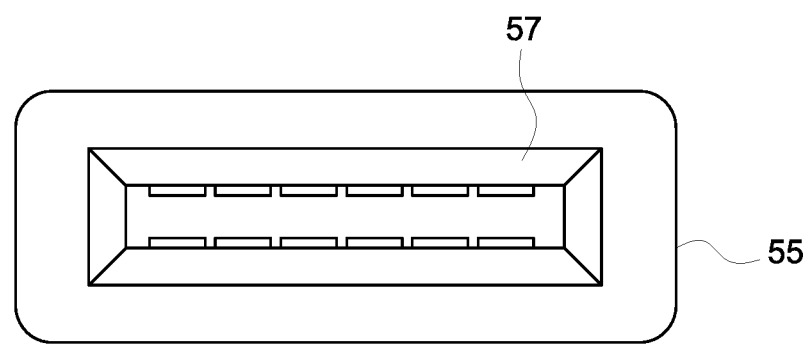
FIG. 16 illustrates a top view of the cassette of FIG. 13.
Figure 17:
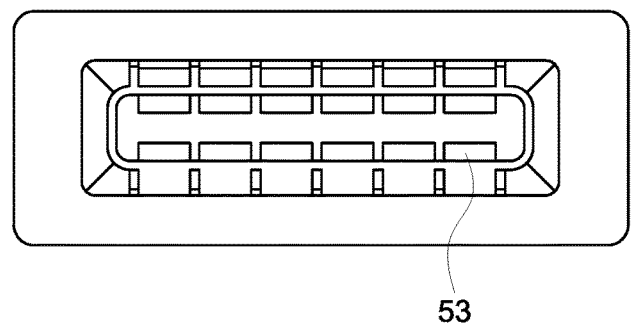
FIG. 17 illustrates a bottom view of the cassette of FIG. 13.
Figure 18:
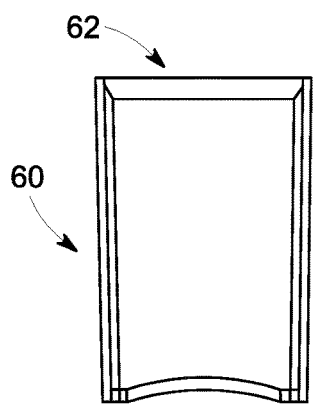
FIG. 18 illustrates a front view of an outer cover of the pour cassette format rapid diagnostic testing device of FIG. 12.
Figure 19:
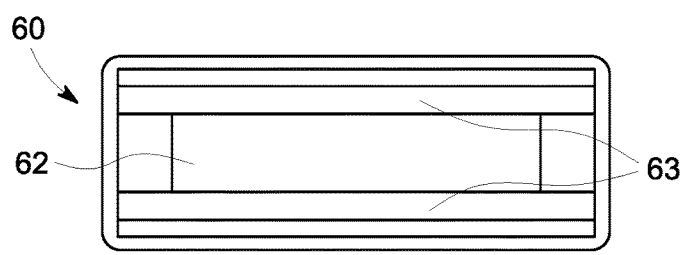
FIG. 19 illustrates a top view of the outer cover of FIG. 18.
Figure 20:
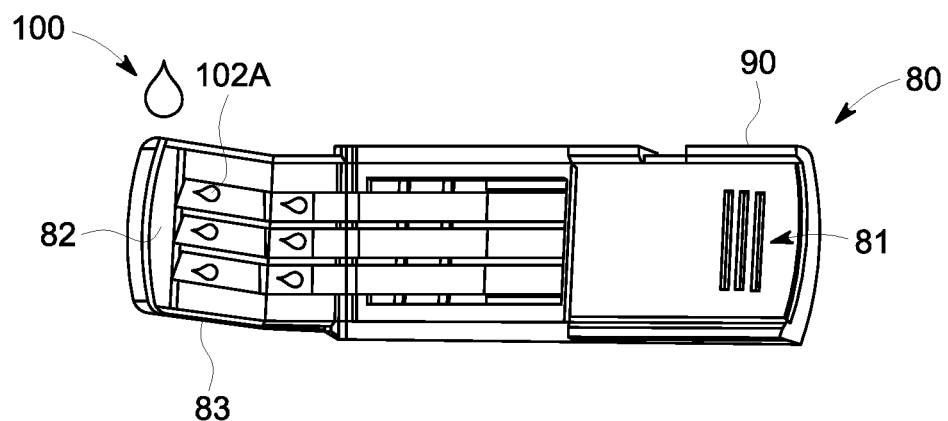
FIG. 20 illustrates a top view of a cassette format rapid diagnostic testing device according to an exemplary embodiment of the present invention.

As best shown in FIG. 16, the opening 56 may be formed in a funnel shape 57 for ease of introduction of the body fluid 100 into the cassette 50.

While the cassette 50 includes six test strip slots 51 on each side thereof, for a total capacity of twelve test strips, fewer or lesser number of test strip slots 51 may be included on the cassette 50. Like the testing device 10 described above, the cassette 50 may include one dripping hole 53 for each of the test strip slots 51.

The outer cup 60 can include an opening 62 for receiving the cassette 50. A compression pad 63 may be disposed on an inside surface of the outer cup 60. The compression pad 63 may be disposed to align adjacent the conjugate pad 42 of the test strip 40 when the test strip 40 is disposed on the cassette 50 and the cassette 50 is placed in the outer cup 60, similar to the compression ring 30 on testing device 10. The compression pad 63 can provide another driving force to help drive all of the gold colloid 43 from the test strip 40 as the stream 102 is directed onto the sample pad 41. The compression pad 63 may be sized to provide a gap between the compression pad 63 and the conjugate pad 42. This gap may be optimized to match with the force of the stream 102 to completely drive all of the gold colloid 43 out of the conjugate pad 42 within seconds.

While not shown in the Figures, the outer cup 60 may include a cover, similar to the cap 11 describe above with respect to testing device 10.

Referring now to FIGS. 20 through 26, when specimen collection volume is not enough for pouring (such as saliva, blood and serum), it can be transferred drop by drop into a sampling inlet 82 of a cassette type testing system 80. The testing system 80 can include a top member 81 covering a base 90. Both the top member 81 and the base 90 include a sloped slide portion 85, 91. A body fluid sample 100 may be introduced, typically by pipette, into the sampling inlet 82 formed between the sloped slide portions 85, 91, collectively referred to as a slide 83, of the top member 81 and the base 90. The body fluid sample 100 may slide down the slide 83 as a fluid stream 102A to impinge upon the sample pad 41 (not shown, see FIG. 2) of a test strip. This provides an alternative stream force similar to the pouring cassette testing system 70 described above. The slide 83 can be designed an at appropriate angle and length to generate enough driving force to simultaneously release the gold colloids onto the membrane. This angle can be from about 30 to about 80 degrees, typically about 60 degrees and the length of the slide may be from about 10 mm to about 30 mm, typically about 20 mm.

Figure 21:
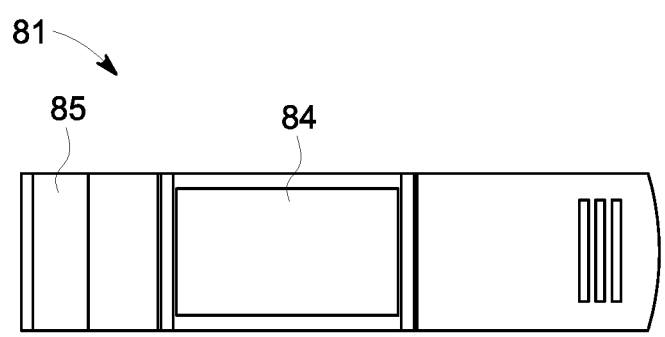
FIG. 21 illustrates a top view of a top member of the cassette format rapid diagnostic testing device of FIG. 20.
Figure 22:
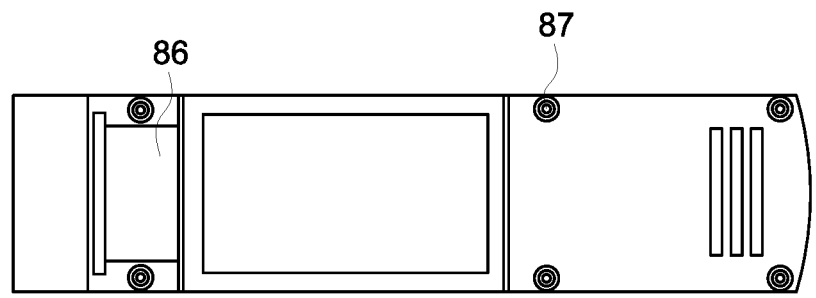
FIG. 22 illustrates a bottom view of the top member of FIG. 21.
Figure 23:
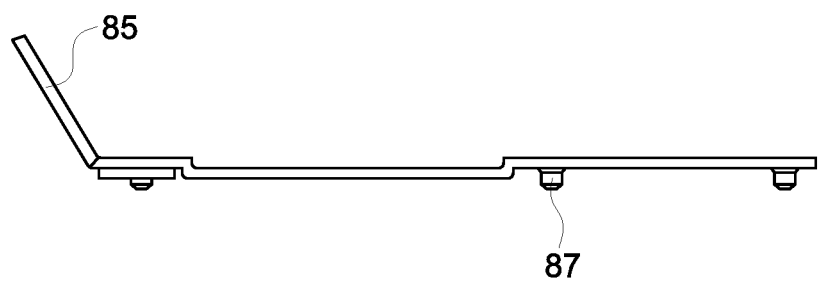
FIG. 23 illustrates a side view of the top member of FIG. 21.
Figure 24:
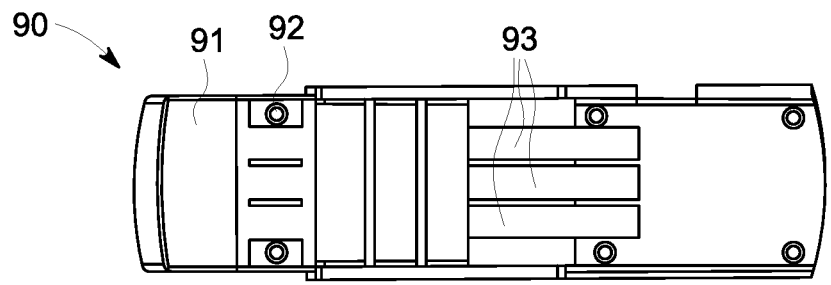
FIG. 24 illustrates a top view of a base member of the cassette format rapid diagnostic testing device of FIG. 20.
Figure 25:
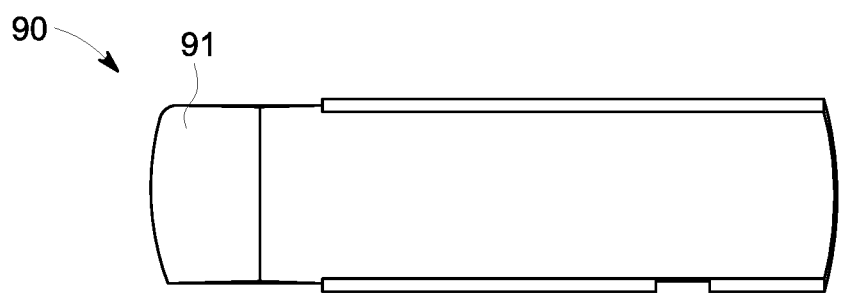
FIG. 25 illustrates a bottom view of the base member of FIG. 24.
Figure 26:
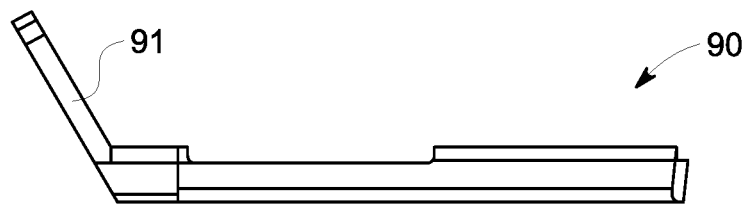
FIG. 26 illustrates a side view of the base member of FIG. 24.

As shown in FIGS. 21 and 22, the top member 81 can include a window 84 for conveniently reading the results shown on the test strips (not shown). Pins 87 may extend from the top member 81 to ensure proper placement of the top member 81 onto the base 90 by aligning the pins 87 into pin holes 92 (see FIG. 24) formed in the base 90. A compression pad 86 may be disposed to extend downward from the top member 81. The compression pad 86 provides a gap between the conjugate pad of the test strip and the compression pad 86. This gap, as described above, may be optimized to provide a further driving force to match with the forward force of the stream 102A to drive all the gold colloid out of the conjugate pad within seconds.

The base 90 can include a plurality of strip slots 93 for receiving a test strip (not shown) therein. The test strips used in the testing device 80 may be similar to those described above in FIG. 2, for example. While three such strip slots 93 are shown, the number of strip slots 93 may vary from a single strip slot to several, depending on the particular application.

Depending on the analyte being tested and the condition of the fluid specimen, many of the above embodiments have been found to achieve an accuracy of at least 99.99%.

In addition, because a result is obtained so quickly, typically within 1 minute, the test does not require additional buffers or other methods to halt the reaction. With both of the testing devices 10, 70, a user simply places the body fluid 100 into the inner portion—either the inner cup 20 or the pour cassette 50—and the fluid exits dripping holes 21, 53 as a stream 102, impacting the sample pad 41 of the test strip 40. With testing device 80, the user can place the body fluid 100 into the sampling inlet 82, where a sloped surface or slide 91 provides the stream 102A of fluid toward the sample pad 41 of the test strip. The stream 102 provides a downward flow, which collects in a reservoir formed in bottom of the outer cup 10, 60. The streams 102, 102A provide an upward flow, which flows through the conjugate pad 42 to force the gold colloid 43 off the conjugate pad 42 and onto the membrane 44. Also, with each of the testing devices 10, 70, 80, a compression member, such as compression ring 30, compression pad 63 and compression pad 86, provides a suitable compression against the conjugate pad 42 to assist in the uniform and rapid release of all of the gold colloid 43 form the conjugate pad 42.

While the above describes a test strip with the gold colloid of antibody 43 disposed on the conjugate pad and the antigen test line 46 disposed on the membrane 44, the actual test conditions may vary as may be understood in the art.

Those skilled in the art will readily recognize, in light of and in accordance with the teachings of the present invention, that any of the foregoing steps may be suitably replaced, reordered, removed and additional steps may be inserted depending upon the needs of the particular application. Moreover, the prescribed method steps of the foregoing embodiments may be implemented using any physical and/or hardware system that those skilled in the art will readily know is suitable in light of the foregoing teachings. Thus, the present invention is not limited to any particular tangible means of implementation.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

Many alterations and modifications may be made by those having ordinary skill in the art without departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different ones of the disclosed elements.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a sub combination.

Insubstantial changes from the claimed subject matter as viewed by a person with ordinary skill in the art, now known or later devised, are expressly contemplated as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptually equivalent, what can be obviously substituted and also what incorporates the essential idea of the invention.

What is claimed is:

1. A test system for testing a liquid sample for the concentration of at least one analyte, comprising:
    a plurality of test strips, each comprising:
        a sample pad receiving the liquid sample;
        a conjugate pad including a gold colloid of antibody; and
        a membrane including an antigen test line; and
    a test device comprising:
        an outer chamber;
        an inner chamber fitting into the outer chamber, the inner chamber receiving the liquid sample therein;
        a plurality of dripping holes formed in a lower portion of the inner chamber, the plurality of dripping holes permitting the liquid sample introduced to the inner chamber to flow as a stream out of the inner chamber and onto the sample pad of each of the plurality of test strips;
        a plurality of test strip slots retaining the plurality of test strips therein; and
        a compressing member positioned adjacent conjugate pad of the test strip.

2. The device of claim 1, wherein each of the plurality of dripping holes has a width no less than a width of the test strip.

3. The device of claim 1, further comprising a reservoir formed in a bottom portion of the outer chamber.

4. The device of claim 3, wherein the stream impacts the sample pad at an angle from about 70 to about 110 degrees.

5. The device of claim 4, wherein the angle provides an upward flow, moving from the sample pad toward the conjugate pad, and a downward flow, moving from the sample pad and into the reservoir.

6. The device of claim 1, wherein the inner chamber is an inner cup having four sides, each side including a portion of the plurality of test strip slots and the compressing member is a compression ring fitting onto pillars formed on an interior surface of the outer chamber.

7. The device of claim 1, wherein the inner chamber is a pour cassette having two test strip mounting sides, each test strip mounting side including a portion of the plurality of test strip slots and wherein the compressing member is a compression pad disposed on opposing internal surfaces of the outer chamber.

8. A device for testing a liquid sample for the concentration of at least one analyte, comprising:
- a base having a base main portion and a base slide portion, the base slide portion extending at a first angle from the base main portion;
- a top member fitting onto the base, the top member having a top member main portion and a top member slide portion, the top member slide portion extending at a second angle from the top member main portion;
- a sampling inlet formed between the base slide portion and the top member slide portion, the sampling inlet receiving the liquid sample therein and directing the liquid sample toward a sample pad of a test strip as a stream when the test strip is disposed in test strip slots of the base; and
- a compressing member positioned adjacent conjugate pad of the test strip when the test strip is placed in the test strip slot.

9. The device of claim 8, further comprising a window in the top member, the window permitting visible access to test strips when disposed in the test strip slots.

* * * * *